US008421043B2

(12) United States Patent
Caiger et al.

(10) Patent No.: US 8,421,043 B2
(45) Date of Patent: Apr. 16, 2013

(54) SOLID STATE RADIATION SOURCE ARRAY

(75) Inventors: Nigel Anthony Caiger, Wookey Hole (GB); Hartley David Selman, Bristol (GB); Shaun Lawrence Herlihy, Chatham (GB)

(73) Assignee: Sun Chemical Corporation, Parsipanny, NJ (US)

( * ) Notice: Subject to any disclaimer, the term of this patent is extended or adjusted under 35 U.S.C. 154(b) by 408 days.

(21) Appl. No.: 12/517,440

(22) PCT Filed: Nov. 30, 2007

(86) PCT No.: PCT/US2007/086094

§ 371 (c)(1),
(2), (4) Date: Oct. 9, 2009

(87) PCT Pub. No.: WO2008/070559

PCT Pub. Date: Jun. 12, 2008

(65) Prior Publication Data

US 2010/0032585 A1 Feb. 11, 2010

(30) Foreign Application Priority Data

Dec. 6, 2006 (GB) .................................. 0624453.7

(51) Int. Cl.
*A61N 5/06* (2006.01)
*G01J 3/10* (2006.01)
*H05G 2/00* (2006.01)

(52) U.S. Cl.
USPC ................. 250/504 R; 250/492.1; 250/491.1; 250/504 H; 433/29

(58) Field of Classification Search ............... 250/492.1, 250/491.1, 504 R, 504 H; 433/29
See application file for complete search history.

(56) References Cited

U.S. PATENT DOCUMENTS

2002/0034594 A1* 3/2002 Shiveley ........................ 427/558
2004/0164325 A1* 8/2004 Siegel ............................ 257/200
2005/0116178 A1* 6/2005 Aguirre et al. ............. 250/492.1
2005/0158687 A1* 7/2005 Dahm ............................. 433/29
2006/0218987 A1* 10/2006 Campman ...................... 73/23.2

FOREIGN PATENT DOCUMENTS

EP 1705520 9/2006
JP 2005015764 1/2005
WO WO 03/096387 11/2003

OTHER PUBLICATIONS

International Search Report and Written Opinion issued for International Application No. PCT/US2007/086094, dated Apr. 29, 2008.

* cited by examiner

*Primary Examiner* — Jack Berman
*Assistant Examiner* — Meenakshi Sahu
(74) *Attorney, Agent, or Firm* — McKenna, Long & Aldridge, LLP.

(57) ABSTRACT

A solid state radiation source array is provided, the array comprising at least one solid state ultraviolet radiation source and at least one solid state infrared radiation source.

21 Claims, 3 Drawing Sheets

SOLID STATE RADIATION SOURCE ARRAY

CROSS REFERENCE TO RELATED APPLICATIONS

This application is the United States national phase filing of the corresponding international application number PCT/US2007/086094, filed on Nov. 30, 2007, which claims priority to and benefit of GB Application No. 0624453.7, filed Dec. 6, 2006, which applications are hereby incorporated by reference in their entirety.

The invention relates to a solid state radiation source array, especially to a solid state radiation source array for use in initiating the curing of an ultraviolet (UV) curable substance.

Traditionally, mercury vapour discharge lamps have been used to generate UV radiation for initiating the curing of UV curable substances such as inks, furniture coatings, lithography resists, adhesives and three-dimensional modelling materials. However, mercury lamps have a number of disadvantages. For instance, mercury lamps are inefficient in their use of energy, only a small percentage of the energy consumed being emitted as UV radiation. Mercury lamps also take time to heat up and cool down and if broken can release mercury which is highly toxic. Accordingly, there is a move away from mercury discharge lamps and toward solid state UV radiation sources such as UV light emitting diodes (LEDs). UV LEDs can be rapidly switched on and off, are more energy efficient than mercury lamps and are safer to use They are also more compact and can be less expensive than mercury lamps. For example, the use of UV LEDs to cure UV curable ink jet inks is disclosed in US 2006/0119686A, US 2005/0128274A, US 2005/0099478A and US 2006/0050122A. The UV LEDs are generally used in the form of an array comprising a large number of individual LED chips. For some applications it is preferred that the array is a mixed array comprising LEDs having differing peak wavelengths in the UV region, thereby providing UV radiation having more than one peak wavelength.

There remains a need for improved devices for initiating the curing of UV curable substances and for improved methods of UV curing.

The invention provides a solid state radiation source array comprising at least one solid state infrared (IR) radiation source and at least one solid state ultraviolet (UV) radiation source. In use of the array of the invention the solid state IR radiation source generates infrared (IR) radiation which heats the UV curable material thereby increasing the temperature of that material and, in consequence, making possible an increase in the rate of the curing reaction and the solid state UV radiation source generates UV radiation which initiates the curing of the UV curable material. Accordingly, the invention aims to provide a simple and easy to use device for curing UV curable materials at an increased rate, thereby making possible an increase in productivity. The array of the invention is, of course, particularly suitable for curing those substances in which the rate of curing is increased at an elevated temperature. In certain applications, for example, the curing of UV curable free radical inkjet inks, the rate of curing is in general insensitive to the temperature of the substance to be cured and the invention is therefore less beneficial in respect of those limited applications. For applications involving cationic ink, however, the rate of curing will be increased with increasing temperature and therefore use of the array of the invention will help make possible an increase in productivity.

The word "array" as used herein refers broadly to any collection of solid state radiation sources. The phrase "solid state radiation source" as used herein refers to any device that generates electromagnetic radiation via the recombination of holes and electrons. The solid state radiation sources may be light emitting diodes, laser diodes, vertical cavity surface emitting lasers, polymer light emitting diodes (LEDs), electroluminescent devices, and any other suitable device which generates electromagnetic radiation via the recombination of holes and electrons. The array may comprise a mixture of different categories of solid state radiation source, for example, a mixture of UV LEDs and IR laser diodes. Optionally, however, all the solid state radiation sources will be of the same category. Semi-conductor devices such as LEDs, laser diodes and vertical cavity surface emitting lasers are preferred. LEDs are particularly preferred due to their commercial availability and good performance characteristics. Preferably, all the solid state radiation sources are LEDs.

The array may include a collection of individual LEDs arranged, for example, in a rectangular pattern. The individual LEDs may have a centre-to-centre separation in the range of from 2 to 5 mm, preferably in the range of from 3 to 4 mm. In a further embodiment, the array may comprise a dense array of LED chips on a common substrate as described further below.

Typically, the array will comprise a plurality of solid state UV radiation sources and a plurality of solid state IR radiation sources. For example, the array may include more than 20, optionally more than 50 solid state UV radiation sources. The array may comprise more than 20, optionally more than 50 solid state IR radiation sources. The array may comprise at least two types of solid state UV radiation source having different peak wavelengths such that the UV radiation emitted by the module has more than one peak wavelength. Using a mixture of solid state UV radiation sources, for example, a mixture of UV LEDs having different peak wavelengths makes possible more efficient curing of certain types of substance. For example, for UV curable ink jet inks it may be desirable to include solid state radiation sources that emit relatively short wave UV radiation to promote curing of the surface layer of the ink and also to include solid state radiation sources which emit a longer wavelength UV radiation which will be transmitted further into the depths of the ink layer. In that way, the array can more effectively cure varying thicknesses of ink layer and inks with varying pigmentation.

The term "solid state UV radiation source" and "UV LED" as used herein refer to solid state radiation sources and LEDs, respectively, having peak emission wavelengths in the UV region of the electromagnetic spectrum, for example, having a peak emission wavelength in the region of from 400 nm to 50 nm. Optionally, the solid state LV radiation source has a peak emission wavelength in the region of from 400 nm to 200 nm, especially preferably in the region of from 400 nm to 300 nm. Preferred solid state UV radiation sources include UV LEDs with peak emission wavelengths of 395 nm and 365 nm. LEDs having a wavelength of 395 nm are widely available. 365 nm LEDs are less common but produce UV radiation which is more closely centred on the absorbance peak of the photo initiators used in certain cationic UV curable materials such as cationic ink jet inks.

The array may comprise at least two types of solid state IR radiation source having different peak wavelengths such that the IR radiation emitted by the array has more than one peak wavelength. For example, the array may comprise solid state radiation sources having peak wavelengths in the near-IR region and also solid state radiation sources having peak emission wavelengths in the mid-IR region.

The terms "solid state JR radiation source" and "IR LED" as used herein refer to solid state radiation sources and LEDs respectively, having peak emission wavelengths in the infrared (IR) region of the electromagnetic spectrum, for example, longer than 700 nm. Optionally, the IR solid state radiation source or sources have peak emission wavelengths of from 700 nm to 100,000 nm, preferably from 700 nm to 10,000 nm and especially preferably in the range of from 700 nm to 2000 nm.

In a preferred embodiment, the array comprises at least one near-IR (NIR) solid state radiation source such as a NIR LED. NIR radiation is selectively absorbed by polar substances and therefore polar substances such as a polar ink applied to a non-polar substrate such as a polyethylene film will be selectively heated by NIR radiation in preference to the non-polar substrate. Accordingly, in this embodiment the array may be used to raise the temperature of a polar substance on a heat sensitive non-polar substrate whilst minimising the temperature rise of the sensitive substrate. NIR LED arrays have previously found application in the detection of errors in the manufacture of semi-conductor microcircuits. Optionally, the NIR solid state radiation source has a peak emission wavelength in the region of from 750 nm to 1400 nm.

In one embodiment the solid state IR radiation sources are substantially evenly dispersed across the array. In that embodiment, the solid state IR radiation sources may be randomly intermingled with the solid state UV radiation sources. Preferably, however, the arrangement of the solid state IR and UV radiation sources forms a repeat pattern. In an alternative embodiment, the solid state IR radiation sources are not evenly dispersed across the array and are instead concentrated in certain areas. The array may have at least first and second areas in which the ratio of solid state IR radiation sources to solid state UV radiation sources is higher in the first area than in the second area. Optionally, the first area comprises solely solid state IR radiation sources and the second area comprises solely solid state UV radiation sources. Such arrays having discrete areas of solid state IR radiation sources and discrete areas of solid state UV radiation sources may be easier to manufacture than arrays having an even distribution of UV and IR solid state radiation sources. It may be desirable for the array to be provided with a diffuser to help reduce unevenness in the nature of the radiation emitted from one area to another in the array.

As mentioned above, the array may comprise one or more dense LED arrays. Such dense LED arrays comprise a plurality of LEDs dispersed in a regular pattern across a common substrate and are described in, for example, WO 03/096387. The dense array may be a mixed dense array comprising both UV and IR LEDs. Alternatively, the array of the invention may comprise one or more dense arrays of UV LEDs and one or more dense arrays of IR LEDs. The array of the invention may comprise at least one solid state UV radiation source and at least one solid state IR radiation source mounted on a common substrate. The array may be provided with cooling means such as a heat sink, fan, or supply of cooling liquid. The array will also typically be provided with circuitry to enable the array to be connected to an external power source. The array may be present as part of a lighting module.

The invention also provides a lighting module comprising at least one solid state UV radiation source and at least one solid state IR radiation source together with the circuitry to provide power to the IR and UV solid state radiation sources. Desirably, the circuitry connects all of the solid state radiation sources of the array to an external power source via a single connector. The lighting module may also comprise control means to control the operation of the solid state radiation sources. For example, the control unit may enable the operator to choose between continuous emission or pulsed emission. Alternatively, the module may comprise connection means for connecting the array to an external control unit. The module may also comprise cooling means to maintain the solid state radiation sources at an acceptable temperature. The cooling means may include one or more of a heat sink, a cooling fan or a conduit for the circulation of cooling liquid. The module may also comprise a housing for the array and associated circuitry and any further optional components such as the cooling means.

Preferably, the solid state radiation sources are LEDs and the lighting module is an LED module. The invention also provides a device for initiating the curing of a UV curable material, the device comprising at least one solid state IR radiation source and at least one solid state UV radiation source. The device may be, for example, a light bar. The light bar may comprise one or more of the lighting modules of the invention. Each lighting module may comprise an array of individual LEDS and/or one or more dense arrays. The device may be a device for curing inks in a printer or print line. For example, the curing device may be a curing station in an ink jet printer such as an ink jet printer for printing CDs and DVDs. The curing device may be a curing station in a flexographic or screen printer. The curing device may be a curing device for the curing of wood and furniture coatings. The curing device may a device for the curing of metal coatings and coil coatings. The curing device may be a curing device for curing three-dimensional prototypes, such as those prototypes which are built-up by ink jet printing successive layers of cationic UV curing ink. The curing device may be a curing device for curing adhesives.

The invention also provides a method of curing a UV curable material which includes the step of exposing the material to a mixture of IR and UV radiation generated by an array, module, or device according to the invention. The method may be a method of curing an ink or coating including metal, wood and furniture coatings, adhesives or it may be a method of three-dimensional modelling. In a preferred embodiment, the method is a method of curing a UV curable ink such as an ink jet ink and the array module or device is located in a printer or print line.

Embodiments of the invention will now be described for the purpose of illustration only with reference to the following drawings in which:

FIG. 1*a* shows in schematic form an array according to the invention;

FIG. 1*b* shows in schematic form a cross-section through the array of FIG. 1*a* along line A to A;

Figure 1A:
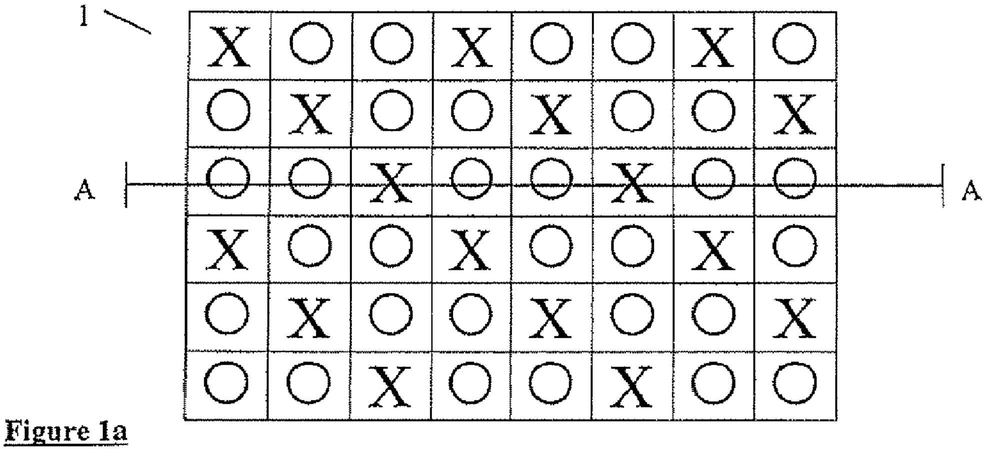

FIG. 1*a* shows a view from the front of a solid state radiation source array 1 according to the invention. The array comprises 40 LEDs arranged in a rectangular 8×6 grid. The LED chips are mounted on a common substrate as a dense LED array. The separation between each LED and its immediate neighbouring LEDs is 2 mm and the array has a nominal length of 16 mm and a nominal width of 12 mm. In FIG. 1*a* each X depicts a NIR LED chip and each ○ depicts a UV LED chip. As can be seen from FIG. 1*a*, the IR chips are evenly spread across the surface of the array in a repeating pattern.

Figure 1B:
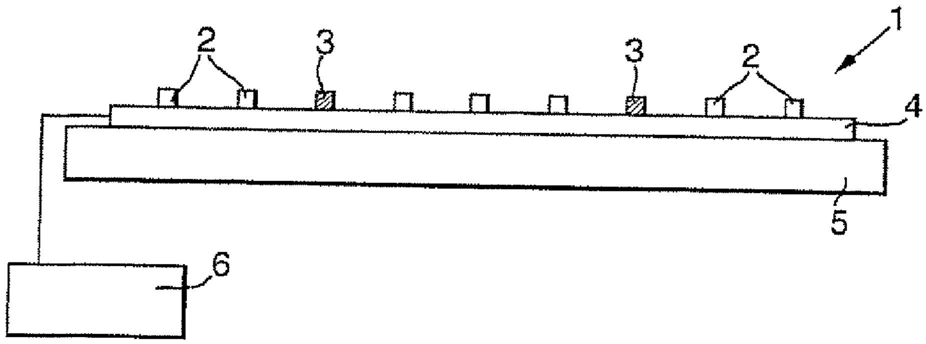

FIG. 1*b* depicts a cross-section through the array of FIG. 1*a* along the lines A to A. The UV LEDs 2 and the IR LEDs 3 are mounted on a common substrate 4 which is bonded with adhesive to a heat sink 5. The chip array 1 is connected via circuitry to a power source 6.

In an alternative embodiment, the array shown in FIG. 1*a* could comprise individual LEDs such that each X would be an individual IR LED and each ○ would represent an individual UV LED. In that embodiment the distance between neighbouring LEDs may be of the order of 3 mm and the length of the array may therefore be around 30 mm and the width may be around 15 mm. The individual LEDs would be connected by wiring circuitry to a common power source. Suitable IR LEDs including N IR LEDs are available from Epitex Inc of Japan. For example, high power NIR LEDs of peak emission wavelength of 870 nm and 850 nm are available from Epitex.

Figure 2:
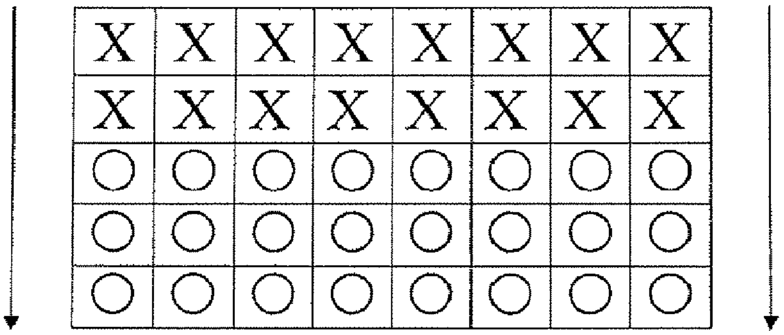
FIG. 2 shows a second array according to the invention.

FIG. 2 shows an alternative solid state radiation source array according to the invention in which the IR LEDs represented by X are located in two rows on one long side of the array and UV LEDs depicted with a ○ are located in the remaining three rows. In this embodiment, the IR LEDs are not evenly dispersed across the array but are instead confined in a certain area located along one long side of the array (the uppermost side as shown in FIG. 2) which area comprises solely IR LEDs. The rest of the array defines a second area which comprises solely UV LEDs. When used for curing a coating applied to a substrate that is moving relative to the array in the direction shown by the arrows, the substrate and coating will pass first under the IR LEDs which will heat the coating to an elevated temperature and then pass under the UV LEDs which will initiate the curing of the coating.

In an alternative embodiment, the region of JR LEDs may comprise a small number of UV LEDs and/or the region of UV LEDs may comprise a small number of IR LEDs. It will furthermore be apparent to the skilled person that the arrays of the invention could comprise any number of LEDs arranged in any pattern and that the rectangular patterns shown in the Figures are for the purpose of illustration only.

Figure 3:
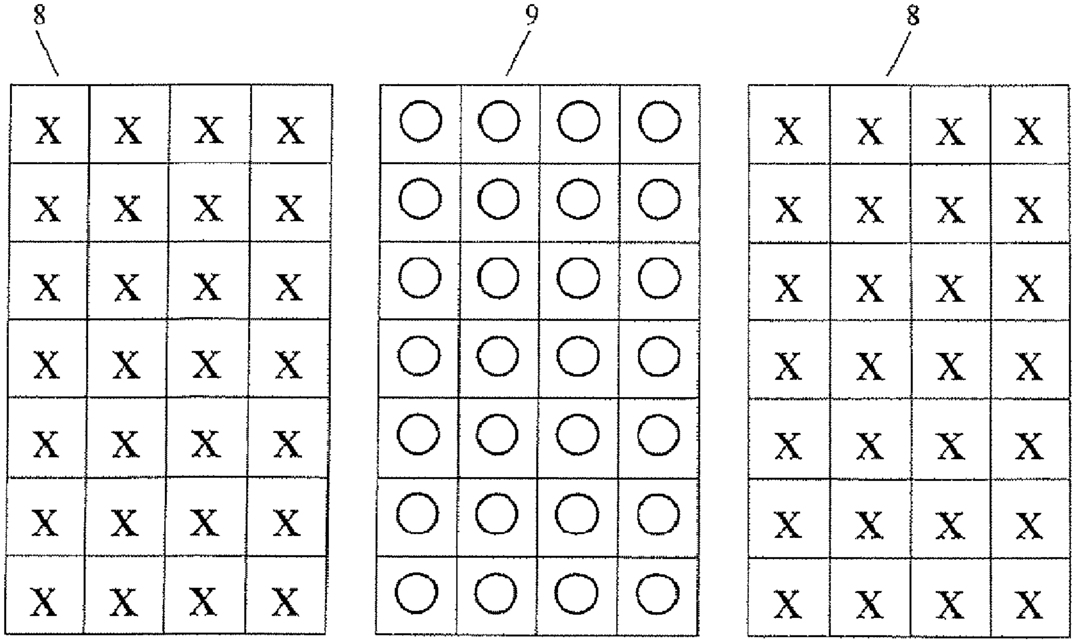
FIG. 3 shows a third array according to the invention.

FIG. 3 shows an array according to the invention comprising three dense arrays, each dense array being a rectangular pattern of 7×4 LEDs. The three dense arrays are arranged in a row with the outermost arrays 8 comprising only IR LEDs and the central dense array 9 comprising only UV LEDs. Typically, the substrate would move from left to right or vice versa relative to the arrays to allow for even coverage of UV and IR radiation over the substrate. The arrangement shown in FIG. 3 could be, for example, mounted on a print head which scans from side to side across the substrate. Once again, it will be apparent to the skilled person that the array shown in FIG. 3 could comprise any number of dense arrays or indeed the dense arrays may be replaced by arrays of individual LEDs. Furthermore, each dense array or array of individual LEDs could comprise a mixture of UV and IR LEDs. However, the arrangement depicted in FIG. 3 in which each dense array includes either IR LEDs or UV LEDs but not both may have the advantage of simplicity of manufacture.

Figure 4:
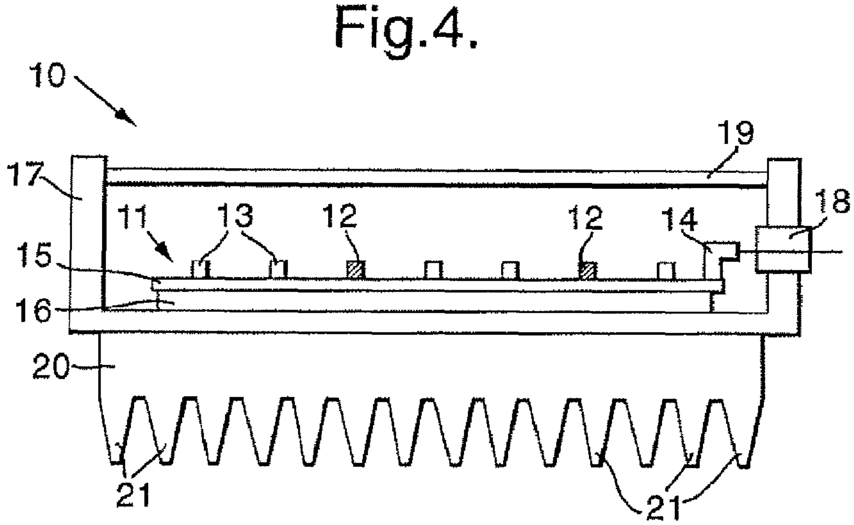
FIG. 4 shows a cross-section through a lighting module according to the invention.

FIG. 4 shows a cross-section through a fighting module 10 according to the invention. The module 10 comprises an array 11 which is a mixed array of IR LEDs 12 and UV LEDs 13. At one side of the array is a power distribution bus 14. The array is mounted on a common substrate 15 which is bonded by a layer of thermally conductive adhesive 16 to a housing 17 which extends around the back and the sides of the array 11. The housing 17 is provided with an electrical connection unit 18 by which the power bus 14 is connected to an external power source (not shown in FIG. 4). The external power source in not a part of the module shown in FIG. 4. The module 10 is also provided with an optical window 19 which is mounted in the housing 17 such that the radiation generated by the array passes out through the window 19. The material of the window 19 is chosen to be substantially transparent to the UV and IR radiation emitted by the array. The optical window 19 could also incorporate a diffuser to ensure an even distribution of the radiation generated by the LEDs 12 and 13. Alternatively, the window 19 could incorporate lens optics to provide focusing of the radiation generated by the array. On the opposite side of the housing a heat sink 20 provided with cooling fans 21 is mounted.

The lighting module shown in FIG. 4 comprises one dense array 11 of LEDs. In an alternative embodiment the lighting module could comprise an array having more than one dense array such as the arrangement shown in FIG. 3 or alternatively could comprise one or more sub-arrays of individual LEDs.

Figure 5:
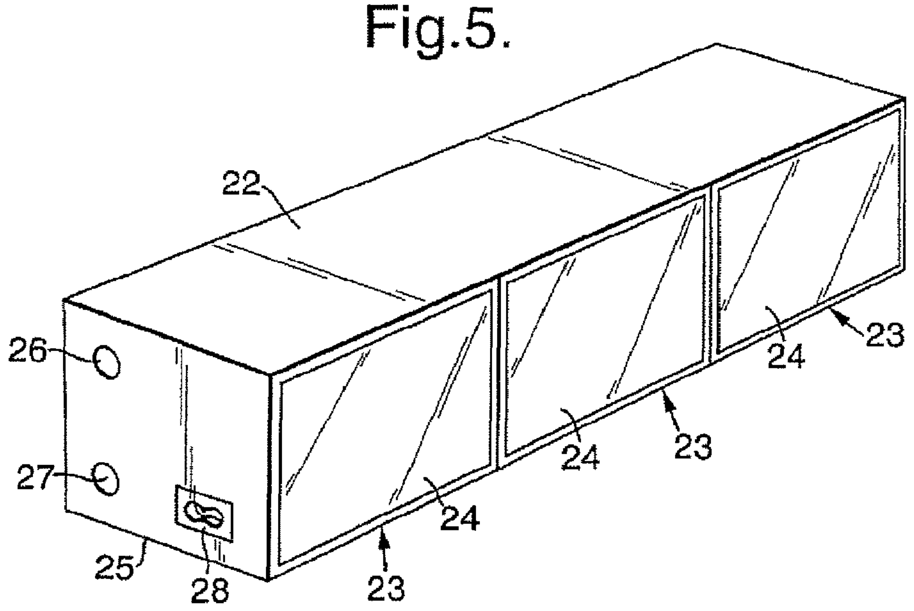
FIG. 5 shows a device for curing a UV curable substance according to the invention.

FIG. 5 shows a device for curing a UV curable substance according to the invention in the form of a light bar 22. The light bar 22 comprises three lighting modules 23 arranged side-by-side with the front window 24 of each lighting module 23 facing forwards from the same side of the light bar 22. The light bar 22 includes a housing 25 which contains the three lighting modules 23 and is provided at one end with ports 26 and 27 for the inflow and outflow respectively of a cooling fluid. The ports 26 and 27 are connected to conduits on the inside of the light bar (not shown in FIG. 5) which carry the cooling fluid around the fins of the heat sinks of the individual lighting modules 23. At the same end of the light bar 22 the housing 25 is provided also with a connector 28 by which the light bar can be connected to an external power source. Connector 28 is connected on the interior of the light bar 22 to a wiring loom which distributes electrical power to the individual lighting modules 23. At the rear of the light bar 22 the housing 25 is provided with threaded studs (not shown in FIG. 5) by which the light bar can be fixed in place, for example, at a curing station in a furniture coating line or on the end of a robotic arm at a curing station in an automotive paint shop.

It will be apparent to the skilled person that many variations of the invention are possible. For example, in place of the LEDs shown in FIGS. 1*a* to 5 laser diodes or polymer light emitting diodes may be used instead. For ascertaining the scope of the invention reference should be made to the appended claims.

The invention claimed is:

1. A solid state radiation source array comprising at least one solid state ultraviolet radiation source having a peak emission wavelength in the 300 to 400 nm range and at least one solid state infrared radiation source, wherein said array is capable of curing UV curable inks and coatings.

2. An array as claimed in claim 1 in which the solid state ultraviolet radiation sources and the solid state infrared radiation sources are light emitting diodes and the array is a light emitting diode array.

3. An array as claimed in claim 1 which comprises a plurality of solid state ultraviolet radiation sources and a plurality of solid state infrared radiation sources.

4. An array as claimed in claim 1 which comprises at least two types of solid state ultraviolet radiation source having different peak wavelengths such that the ultraviolet radiation emitted by the array has more than one peak wavelength.

5. An array as claimed in claim 1 in which the at least one solid state infrared radiation source is a solid state near-infrared radiation source.

6. An array as claimed in claim 1 which comprises at least two types of solid state infrared radiation source having different peak wavelengths such that the infrared radiation emitted by the array has more than one peak wavelength.

7. An array as claimed in claim 1 which comprises at least one solid state ultraviolet radiation source and at least one solid state infrared radiation source mounted on a common substrate.

8. An array as claimed in claim 7 which comprises a plurality of solid state infrared radiation sources and a plurality of solid state infrared radiation sources mounted on a common substrate.

9. An array as claimed in claim 1 in which the solid state infrared radiation sources are substantially evenly dispersed across the array.

10. An array as claimed in claim 1 in which the solid state infrared radiation sources are not evenly dispersed across the array.

11. An array as claimed in claim 10 which has at least first and second areas in which the ratio of solid state infrared radiation sources to solid state ultraviolet radiation sources is higher in the first area than in the second area.

12. An array as claimed in claim 11 in which the first area comprises solely solid state infrared radiation sources and the second area comprises solely solid state ultraviolet radiation sources.

13. A light emitting diode array comprising a plurality of ultraviolet light emitting diodes having a peak emission wavelength in the 300 to 400 nm range and a plurality of infrared light emitting diodes, wherein said array is capable of curing UV curable inks and coatings.

14. A lighting module comprising an array with at least one solid state ultraviolet radiation source having a peak emission wavelength in the 300 to 400 nm range and at least one solid state infrared radiation source, together with circuitry to provide power to the infrared and ultraviolet solid state radiation sources, wherein said array is capable of curing UV curable inks and coatings.

15. A module as claimed in claim 14 in which the solid state radiation sources are light emitting diodes.

16. A light emitting diode module comprising a light emitting diode array including a plurality of ultraviolet light emitting diodes having a peak emission wavelength in the 300 to 400 nm range and a plurality of infrared light emitting diodes, a housing for the array and cooling means for carrying heat away from the light emitting diodes, wherein said array is capable of curing UV curable inks and coatings.

17. A device for initiating the curing of an ultraviolet curable material, the device comprising an array with at least one solid state infrared radiation source and at least one solid state ultraviolet radiation source having a peak emission wavelength in the 300 to 400 nm range.

18. A device as claimed in claim 17 which is a light bar.

19. A method of curing an ultraviolet curable material including the step of exposing the material to a mixture of infrared and ultraviolet radiation generated by an array according to claim 1, a module according to claim 14, or a device according to claim 17.

20. A method according to claim 19 in which the material is an ultraviolet curable ink jet ink and the array, module or device is located in a curing station in a printer or print line.

21. An array as claimed in claim 1, wherein said at least one solid state infrared radiation source has a peak emission wavelength of 700 to 2,000 nm.

* * * * *